United States Patent
Negre

(10) Patent No.: US 11,535,681 B2
(45) Date of Patent: Dec. 27, 2022

(54) SICKLED BETA GLOBIN ANTIBODIES

(71) Applicant: bluebird bio, Inc., Cambridge, MA (US)

(72) Inventor: Olivier Negre, Cambridge, MA (US)

(73) Assignee: Bluebird Bio, Inc., Cambridge, MA (US)

( * ) Notice: Subject to any disclaimer, the term of this patent is extended or adjusted under 35 U.S.C. 154(b) by 263 days.

(21) Appl. No.: 16/771,411

(22) PCT Filed: Dec. 14, 2018

(86) PCT No.: PCT/US2018/065782
§ 371 (c)(1),
(2) Date: Jun. 10, 2020

(87) PCT Pub. No.: WO2019/118892
PCT Pub. Date: Jun. 20, 2019

(65) Prior Publication Data
US 2020/0347150 A1    Nov. 5, 2020

Related U.S. Application Data

(60) Provisional application No. 62/599,260, filed on Dec. 15, 2017.

(51) Int. Cl.
*C07K 16/34* (2006.01)
(52) U.S. Cl.
CPC ........ *C07K 16/34* (2013.01); *C07K 2317/565* (2013.01); *C07K 2317/622* (2013.01)
(58) Field of Classification Search
None
See application file for complete search history.

(56) References Cited

U.S. PATENT DOCUMENTS

| | | |
|---|---|---|
| 4,752,583 A | 6/1988 | Jensen et al. |
| 2011/0117670 A1* | 5/2011 | Walker ............ G01N 33/531 530/387.9 |
| 2016/0116489 A1 | 4/2016 | Cao et al. |

FOREIGN PATENT DOCUMENTS

WO    WO 2017/139478 A1    8/2017

OTHER PUBLICATIONS

Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Edwards et al., J Mol Biol. Nov. 14, 2003;334(1):103-18.*
Lloyd et al., Protein Eng Des Sel. Mar. 2009;22(3):159-68. doi: 10.1093/protein/gzn058. Epub Oct. 29, 2008.*
Goel et al., J Immunol. Dec. 15, 2004;173(12):7358-67.*
Kanyavuz et al., Nat Rev Immunol. Jun. 2019;19(6):355-368. doi: 10.1038/S41577-019-0126-7.*
Curd et al., J Biol Chem. Mar. 10, 1976;251(5):1290-5.*
Boerner et al., "Production of antigen-specific human monoclonal antibodies from in vitro-primed human splenocytes," J Immunol, Jul. 1, 1991, 147 (1) 86-95.
Brodeur et al., Monoclonal Antibody Production Techniques and Applications, pp. 51-63 (Marcel Dekker, Inc., New York, 1987).
Bruggemann et al., "Designer mice: the production of human antibody repertoires in transgenic animals," Year in Immunol., 7: 33-40 (1993).
International Search Report and Written Opinion dated Mar. 11, 2019, for International Application No. PCT/US2018/065782, 8 pages.
Jakobovits et al., "Analysis of homozygous mutant chimeric mice: deletion of the immunoglobulin heavy-chain joining region blocks B-cell development and antibody production," PNAS Mar. 15, 1993, 90 (6) 2551-2555.
Jakobovits et al., "Germ-line transmission and expression of a human-derived yeast artificial chromosome," Nature, 362: 255 (1993).
Kozbor et al., "A human hybrid myeloma for production of human monoclonal antibodies," J Immunol Dec. 1, 1984, 133 (6) 3001-3005.
Pluckthun, "Antibodies from *Escherichia coli*," The Pharmacology of Monoclonal Antibodies, vol. 113, Rosenburg and Moore eds., (Springer-Verlag, New York, 1994), pp. 269-315.
Young et al., "The NH2-terminal Region of the Sickle Hemoglobin β Chain," The Journal of Biological Chemistry, Oct. 25, 1976, vol. 251, No. 20, pp. 6431-6438.

* cited by examiner

*Primary Examiner* — Michael Szperka
(74) *Attorney, Agent, or Firm* — Morse, Barnes-Brown & Pendleton, P.C.; Lisa M. Warren, Esq.; Erin E. Bryan, Esq.

(57) ABSTRACT

The invention generally provides improved anti-sickled-globin antibodies and fragments thereof. In particular embodiments, the antibody or antigen binding fragment thereof recognizes the βs, Glu6Val mutation. In various embodiments, the invention provides a conjugate comprising an anti-βs-globin antibody or antigen binding fragment thereof and a detectable label. In particular embodiments, a hybridoma comprising an anti-βs-globin antibody contemplated herein is provided.

5 Claims, 5 Drawing Sheets
Specification includes a Sequence Listing.

SICKLED BETA GLOBIN ANTIBODIES

CROSS REFERENCE TO RELATED APPLICATIONS

This application claims the benefit under 35 U.S.C. § 119(e) of U.S. Provisional Application No. 62/599,260, filed Dec. 15, 2017, each of which is incorporated by reference herein in its entirety.

STATEMENT REGARDING SEQUENCE LISTING

The Sequence Listing associated with this application is provided in text format in lieu of a paper copy and is hereby incorporated by reference into the specification. The name of the text file containing the Sequence Listing is BLBD_093_01WO_ST25.txt. The text file is 9 KB, was created on Dec. 13, 2018, and is being submitted electronically via EFS-Web, concurrent with the filing of the specification.

BACKGROUND

Technical Field

The present invention relates to sickled β-globin (βS) antibodies or antigen binding fragments thereof.

Description of the Related Art

Hemoglobinopathies are the most prevalent inherited diseases worldwide and result from abnormal β-globin synthesis or structure. Hemoglobinopathies are a diverse group of inherited blood disorders that involve the presence of abnormal hemoglobin molecules resulting from alterations in the structure and/or synthesis of hemoglobin. Normally, hemoglobin consists of four protein subunits: two subunits of β-globin and two subunits of α-globin. Each of these protein subunits is attached (bound) to an iron-containing molecule called heme; each heme contains an iron molecule in its center that can bind to one oxygen molecule. Hemoglobin within red blood cells binds to oxygen molecules in the lungs. These cells then travel through the bloodstream and deliver oxygen to tissues throughout the body. The most common hemoglobinopathies include sickle cell disease, β-thalassemia, and α-thalassemia.

Sickle cell disease includes any symptomatic anemic condition which results from sickling of red blood cells. Sickle cell anemia βS/βS, a common form of sickle cell disease (SCD), is caused by Hemoglobin S (HbS). HbS is a tetramer of two βS globin sununits and two α-globin subunits. HbS is generated by replacement of glutamic acid (E) with valine (V) at position 6 in β-globin, noted as Glu6Val or E6V. The E6V position refers to the amino acid position in the final protein product because the first amino acid is removed after translation. Replacing glutamic acid with valine causes the abnormal HbS subunits to stick together and form long, rigid molecules that bend red blood cells into a sickle (crescent) shape. The sickle-shaped cells die prematurely, which can lead to a shortage of red blood cells (anemia). In addition, the sickle-shaped cells are rigid and can block small blood vessels, causing severe pain and organ damage.

BRIEF SUMMARY

The invention generally provides improved anti-sickled-globin antibodies and fragments thereof. The antibodies or antigen binding fragments thereof can be used to detect $\beta^S$. $\beta^S$ is generated by replacement of glutamic acid (E) with valine (V) at position 6 in β-globin, noted as Glu6Val or E6V. The E6V position refers to the amino acid position in the final protein product because the first amino acid is removed after translation.

In various embodiments, the anti-$\beta^S$-globin antibody or antigen binding fragment thereof comprises a variable light chain sequence comprising CDRL1-CDRL3 sequences set forth in SEQ ID NOs: 1-3, and a variable heavy chain sequence comprising CDRH1-CDRH3 sequences set forth in SEQ ID NOs: 4-6.

In particular embodiments, the antibody or antigen binding fragment thereof recognizes the $\beta^S$, E6V mutation.

In certain embodiments, the anti-$\beta^S$-globin antibody or antigen binding fragment that binds the human $\beta^S$-globin polypeptide is an scFv.

In particular embodiments, the anti-$\beta^S$-globin antibody or antigen binding fragment thereof comprises one or more light chain CDRs as set forth in any one of SEQ ID NOs: 1-3 and/or one or more heavy chain CDRs as set forth in any one of SEQ ID NOs: 4-6.

In some embodiments, the anti-$\beta^S$-globin antibody or antigen binding fragment thereof comprises a variable light chain sequence as set forth in SEQ ID NO: 7 and/or a variable heavy chain sequence as set forth in SEQ ID NO: 8.

In various embodiments, a conjugate, comprises an anti-$\beta^S$-globin antibody or antigen binding fragment thereof contemplated herein and a means for detection.

In various embodiments, a conjugate, comprises an anti-$\beta^S$-globin antibody or antigen binding fragment thereof contemplated herein and a detection means.

In various embodiments, a conjugate, comprises an anti-$\beta^S$-globin antibody or antigen binding fragment thereof contemplated herein and a detectable label.

In some embodiments, the detectable label is selected from the group consisting of: a hapten, a fluorescent dye, a fluorescent protein, a chromophore, a metal ion, a gold particle, a silver particle, a magnetic particle, a polypeptide, an enzyme, a luminescent compound, or an oligonucleotide.

In particular embodiments, the detectable label is a fluorescent dye selected from the group consisting of: Oregon Green®, Pacific Blue™, Pacific Orange™, Pacific Green™, Cascade Blue™, Cascade Yellow™, Lucifer Yellow™, Marina Blue™, and Texas Red® (TxRed).

In certain embodiments, the detectable label is an AlexaFluor®(AF) dye selected from the group consisting of: AF350, AF405, AF488, AF500, AF514, AF532, AF546, AF555, AF568, AF594, AF610, AF633, AF635, AF647, AF680, AF700, AF710, AF750, AF790, and AF800.

In some embodiments, the detectable label is a QDot® selected from the group consisting of: Qdot®525, Qdot®565, Qdot®585, Qdot®605, Qdot®655, Qdot®705, and Qdot®800.

In particular embodiments, the detectable label is a DyLight™ Dye (DL) selected from the group consisting of: DL549, DL649, DL680, and DL800.

In certain embodiments, the detectable label is a hapten selected from the group consisting of: fluorescein or a derivative thereof, fluorescein isothiocyanate, carboxyfluorescein, dichlorotriazinylamine fluorescein, digoxigenin, dinitrophenol (DNP), trinitrophenol (TNP), and biotin.

In particular embodiments, the detectable label is a Cy Dye selected from the group consisting of: Cy2, Cy3, Cy3.5, Cy5, Cy5.5, Cy7, and Cy 7.5.

In some embodiments, the detectable label is a fluorescent molecule selected from the group consisting of: Phycoerythrin (PE, R-Phycoerythrin (RPE)), B-Phycoerythrin (BPE), Peridinin Chlorophyll (PerCP), Allophycocyanin (APC), and C-Phycocyanin.

In particular embodiments, the detectable label is a fluorescent dye selected from the group consisting of: Atto 390, Atto 425, Atto 465, Atto 488, Atto 495, Atto 514 Atto 520, Atto 532, Atto 550, Atto 565, Atto 590, Atto 594, Atto 610, Atto 620, Atto 633, Atto 647, Atto 655, Atto 665, Atto 680, Atto 700, Atto 725, Atto 740, Super Bright™ 436, Super Bright™ 600, Super Bright™ 645, Super Bright™ 702, Super Bright™ 780, Brilliant™ Violet 421, Brilliant™ Violet 480, Brilliant™ Violet 510, Brilliant™ Violet 605, Brilliant Violet™ 650, Brilliant Violet™ 711, Brilliant Violet™ 786, Brilliant™ Ultraviolet 395 (BUV395), Brilliant™ Ultraviolet 496 (BUV496), Brilliant™ Ultraviolet 563 (BUV563), Brilliant™ Ultraviolet 661 (BUV661), Brilliant™ Ultraviolet 737 (BUV737), Brilliant™ Ultraviolet 805 (BUV805), Brilliant™ Blue 515 (BB515), Brilliant™ Blue 700 (BB700) and IR Dye 680, IR Dye 680LT, IR Dye 700, IR Dye 700DX, IR Dye 800, IR Dye 800RS, and IR Dye 800CW.

In certain embodiments, the detectable label is a tandem fluorescent dye selected from the group consisting of: RPE-Cy5, RPE-Cy5.5, RPE-Cy7, RPE-CF594, RPE-AlexaFluor® tandem conjugates; RPE-Alexa610, RPE-TxRed, APC-H7, APC-R700, APC-Alexa600, APC-Alexa610, APC-Alexa750, APC-Cy5, APC-Cy5.5, and APC-Cy7.

In certain embodiments, the detectable label is a fluorescent protein selected from the group consisting of: GFP, eGFP, BFP, CFP, YFP, DsRed, DsRed2, mRFP, mBanana, mOrange, dTomato, tdTomato, mTangerine, mStrawberry, mCherry, mPlum, and mRaspberry.

In particular embodiments, the detectable label is an enzyme selected from the group consisting of: alkaline phosphatase, horseradish peroxidase, luciferase, and β-galactosidase.

In certain embodiments, the detectable label comprises a radionuclide selected from the group consisting of: carbon (14C), chromium (51Cr), cobalt (57Co), fluorine (18F), gadolinium (153Gd, 159Gd), germanium (68Ge), holmium (166Ho), indium (115In, 113In, 112In, mIn), iodine (125I, 123I, 121I), lanthanium (140La), lutetium (177Lu), manganese (54Mn), molybdenum (99 Mo), palladium (103 Pd), phosphorous (32 P), praseodymium (142 Pr), promethium (149Pm), rhenium (186Re, 188Re), rhodium (105Rh), rutheroium (97Ru), samarium (153Sm), scandium (47Sc), selenium (75Se), (85Sr), sulphur (35S), technetium (99Tc), thallium (201Ti), tin (113Sn, 117Sn), tritium (3H), xenon (133Xe), ytterbium (169Yb, 175Yb), and yttrium (90Y).

In particular embodiments, a hybridoma comprising an antibody contemplated herein is provided.

In various embodiment, a polynucleotide encoding an antibody or antigen binding fragment thereof is contemplated.

BRIEF DESCRIPTION OF THE SEQUENCE IDENTIFIERS

Figure 1:
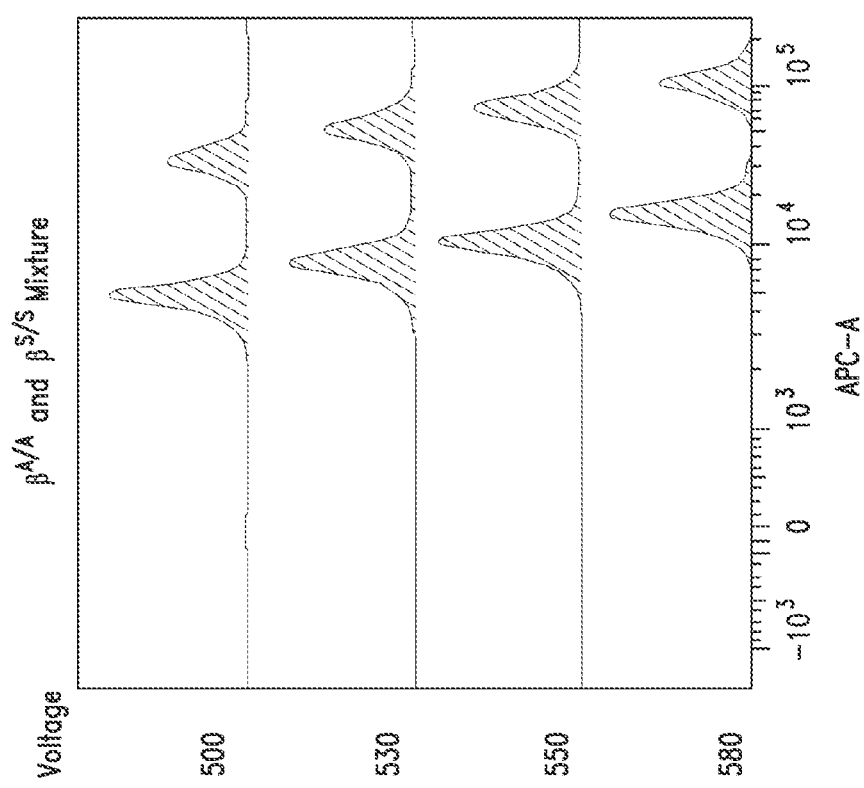
FIG. 1 shows HbS staining of normal and sickled red blood cells with an anti-$\beta^S$ antibody.

SEQ ID NOs: 1-3 set forth exemplary amino acid sequences of light chain CDR sequences.

SEQ ID NOs: 4-6 set forth exemplary amino acid sequences of heavy chain CDR sequences.

SEQ ID NO: 7 sets forth an exemplary variable domain light chain.

SEQ ID NO: 8 sets forth an exemplary variable domain heavy chain.

SEQ ID NO: 9 sets forth a human $\beta^S$-globin amino acid sequence.

SEQ ID NOs: 10-20 set forth the amino acid sequences of various linkers.

DETAILED DESCRIPTION

A. Overview

The invention generally relates to improved anti-βS-globin antibodies and antigen binding fragments thereof, compositions, and diagnostic uses of the same.

βS globin is generated by replacement of glutamic acid (E) with valine (V) at position 6 in β-globin, noted as Glu6Val or E6V.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, N.Y.); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid* The *Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C C Blackwell, eds., 1986); Roitt, *Essential Immunology*, 6th Edition, (Blackwell Scientific Publications, Oxford, 1988); *Current Protocols in Immunology* (Q. E. Coligan, A. M. Kruisbeek, D. H. Margulies, E. M. Shevach and W. Strober, eds., 1991); *Annual Review of Immunology*; as well as monographs in journals such as *Advances in Immunology*.

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

Additional definitions are set forth throughout this disclosure.

C. Antibodies

In particular embodiments, an antibody or antigen binding fragment thereof is provided.

The term "antibody" refers to a binding agent that is a polypeptide comprising at least a light chain or heavy chain immunoglobulin variable region or fragment thereof which specifically recognizes and binds an epitope of an antigen, such as a peptide, lipid, polysaccharide, or nucleic acid containing an antigenic determinant, such as those recognized by an immune cell.

An "isolated antibody or antigen binding fragment thereof" is one which has been identified and separated and/or recovered from a component of its natural environment.

The terms "specific binding affinity" or "specifically binds" or "specifically bound" or "specific binding" or "specifically targets" as used herein, describe binding of an anti-$\beta^{A T87Q}$-globin globin antibody or antigen binding fragment thereof to $\beta^{A T87Q}$-globin at greater binding affinity than background binding. An antibody or antigen binding fragment thereof "specifically binds" to a $\beta^{A T87Q}$-globin polypeptide if it binds to or associates with $\beta^{A T87Q}$-globin with an affinity or $K_a$ (i.e., an equilibrium association constant of a particular binding interaction with units of 1/M) of, for example, greater than or equal to about $10^5$ $M^{-1}$. In certain embodiments, an antibody or antigen binding fragment thereof binds to a target with a $K_a$ greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" antibody or antigen binding fragment thereof have a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater.

Alternatively, affinity may be defined as an equilibrium dissociation constant ($K_d$) of a particular binding interaction with units of M (e.g., $10^{-5}$ M to $10^{-13}$ M, or less). Affinities of antibody or antigen binding fragment thereof contemplated herein can be readily determined using conventional techniques, e.g., by competitive ELISA (enzyme-linked immunosorbent assay), or by binding association, or displacement assays using labeled ligands, or using a surface-plasmon resonance device such as the Biacore T100, which is available from Biacore, Inc., Piscataway, N.J., or optical biosensor technology such as the EPIC system or EnSpire that are available from Corning and Perkin Elmer respectively (see also, e.g., Scatchard et al. (1949) Ann. N.Y. Acad. Sci. 51:660; and U.S. Pat. Nos. 5,283,173; 5,468,614, or the equivalent).

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

An "antigen (Ag)" refers to a compound, composition, or substance that can stimulate the production of antibodies or a T cell response in an animal, including compositions (such as one that includes a cancer-specific protein) that are injected or absorbed into an animal. An antigen reacts with the products of specific humoral or cellular immunity, including those induced by heterologous antigens, such as the disclosed antigens. In particular embodiments, the target antigen is an epitope of a $\beta^{AT87Q}$-globin polypeptide.

An "epitope" or "antigenic determinant" refers to the region of an antigen to which a binding agent binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation.

Antibodies include antigen binding fragments thereof, such as a Camel Ig, a Llama Ig, an Alpaca Ig, Ig NAR, a Fab' fragment, a F(ab')$_2$ fragment, a bispecific Fab dimer (Fab2), a trispecific Fab trimer (Fab3), an Fv, an single chain Fv protein ("scFv"), a bis-scFv, (scFv)$_2$, a minibody, a diabody, a triabody, a tetrabody, a disulfide stabilized Fv protein ("dsFv"), and a single-domain antibody (sdAb, a camelid VHH, Nanobody) and portions of full length antibodies responsible for antigen binding. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, Ill.); Kuby, J., Immunology, 3$_{rd}$ Ed., W. H. Freeman & Co., New York, 1997.

As would be understood by the skilled person and as described elsewhere herein, a complete antibody comprises two heavy chains and two light chains. Each heavy chain consists of a variable region and a first, second, and third constant region, while each light chain consists of a variable region and a constant region. Mammalian heavy chains are classified as α, δ, ε, γ, and μ. Mammalian light chains are classified as λ or κ. Immunoglobulins comprising the α, δ, ε, γ, and μ heavy chains are classified as immunoglobulin (Ig)A, IgD, IgE, IgG, and IgM. The complete antibody forms a "Y" shape. The stem of the Y consists of the second and third constant regions (and for IgE and IgM, the fourth constant region) of two heavy chains bound together and disulfide bonds (inter-chain) are formed in the hinge. Heavy chains γ, α and δ have a constant region composed of three tandem (in a line) Ig domains, and a hinge region for added flexibility; heavy chains μ and ε have a constant region composed of four immunoglobulin domains. The second and third constant regions are referred to as "CH2 domain" and "CH3 domain", respectively. Each arm of the Y includes the variable region and first constant region of a single heavy chain bound to the variable and constant regions of a single light chain. The variable regions of the light and heavy chains are responsible for antigen binding.

Light and heavy chain variable regions contain a "framework" region interrupted by three hypervariable regions, also called "complementarity-determining regions" or "CDRs." The CDRs can be defined or identified by conventional methods, such as by sequence according to Kabat et al. (Wu, T T and Kabat, E. A., J Exp Med. 132(2):211-50, (1970); Borden, P. and Kabat E. A., PNAS, 84: 2440-2443 (1987); (see, Kabat et al., Sequences of Proteins of Immunological Interest, U.S. Department of Health and Human Services, 1991, which is hereby incorporated by reference), or by structure according to Chothia et al (Chothia, C. and Lesk, A. M., J Mol. Biol., 196(4): 901-917 (1987), Chothia, C. et al, Nature, 342: 877-883 (1989)).

Illustrative examples of rules for predicting light chain CDRs include: CDR-L1 starts at about residue 24, is preceded by a Cys, is about 10-17 residues, and is followed by a Trp (typically Trp-Tyr-Gln, but also, Trp-Leu-Gln, Trp-Phe-Gln, Trp-Tyr-Leu); CDR-L2 starts about 16 residues after the end of CDR-L1, is generally preceded by Ile-Tyr, but also, Val-Tyr, Ile-Lys, Ile-Phe, and is 7 residues; and CDR-L3 starts about 33 residues after the end of CDR-L2, is preceded by a Cys, is 7-11 residues, and is followed by Phe-Gly-XXX-Gly (SEQ ID NO:21) (XXX is any amino acid).

Illustrative examples of rules for predicting heavy chain CDRs include: CDR-H1 starts at about residue 26, is preceded by Cys-XXX-XXX-XXX (SEQ ID NO:22), is 10-12 residues and is followed by a Trp (typically Trp-Val, but also, Trp-Ile, Trp-Ala); CDR-H2 starts about 15 residues after the end of CDR-H1, is generally preceded by Leu-Glu-Trp-Ile-Gly (SEQ ID NO:23), or a number of variations, is 16-19 residues, and is followed by Lys/Arg-Leu/Ile/Val/Phe/Thr/Ala-Thr/Ser/Ile/Ala; and CDR-H3 starts about 33 residues after the end of CDR-H2, is preceded by Cys-XXX-XXX (typically Cys-Ala-Arg), is 3 to 25 residues, and is followed by Trp-Gly-XXX-Gly (SEQ ID NO:24).

In one embodiment, light chain CDRs and the heavy chain CDRs are determined according to the Kabat method In one embodiment, light chain CDRs and the heavy chain CDR2 and CDR3 are determined according to the Kabat method, and heavy chain CDR1 is determined according to the AbM method, which is a comprise between the Kabat and Clothia methods, see e.g., Whitelegg N & Rees A R, Protein Eng. 2000 December; 13(12):819-24 and Methods Mol Biol. 2004; 248:51-91. Programs for predicting CDRs are publicly available, e.g., AbYsis (www.bioinf.org.uk/abysis/).

The sequences of the framework regions of different light or heavy chains are relatively conserved within a species, such as humans. The framework region of an antibody, that is the combined framework regions of the constituent light and heavy chains, serves to position and align the CDRs in three-dimensional space. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, the CDRs located in the variable domain of the heavy chain of the antibody are referred to as CDRH1, CDRH2, and CDRH3, whereas the CDRs located in the variable domain of the light chain of the antibody are referred to as CDRL1, CDRL2, and CDRL3. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

Illustrative examples of light chain CDRs include the CDR sequences set forth in SEQ ID NOs: 1-3. Illustrative examples of heavy chain CDRs include the CDR sequences set forth in SEQ ID NOs: 4-6.

References to "$V_L$" or "VL" refer to the variable region of an immunoglobulin light chain, including that of an antibody, Fv, scFv, dsFv, Fab, or other antibody fragment as disclosed herein. Illustrative examples of light chain variable regions include the light chain variable region sequences set forth in SEQ ID NO: 7.

References to "$V_H$" or "VH" refer to the variable region of an immunoglobulin heavy chain, including that of an antibody, Fv, scFv, dsFv, Fab, or other antibody fragment as disclosed herein. Illustrative examples of heavy chain variable regions include the heavy chain variable region sequences set forth in SEQ ID NO: 8.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a mouse. In particular preferred embodiments, an antibody comprises antigen-specific binding domain that is a chimeric antibody or antigen binding fragment thereof.

In preferred embodiments, the antibody is a human antibody (such as a human monoclonal antibody) or fragment thereof that specifically binds to a human $\beta^{AT87Q}$-globin polypeptide. Human antibodies can be constructed by combining Fv clone variable domain sequence(s) selected from human-derived phage display libraries with known human constant domain sequences(s) as described above. Alternatively, human monoclonal antibodies may be made by the hybridoma method. Human myeloma and mouse-human heteromyeloma cell lines for the production of human monoclonal antibodies have been described, for example, by Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991). In addition, transgenic animals (e.g., mice) can be used to produce a full repertoire of human antibodies in the absence of endogenous immunoglobulin production. See, e.g., Jakobovits et al., *PNAS USA,* 90: 2551 (1993); Jakobovits et al., *Nature,* 362: 255 (1993); Bruggermann et al., *Year in Immunol.,* 7: 33 (1993). Gene shuffling can also be used to derive human antibodies from non-human, e.g., rodent antibodies, where the human antibody has similar affinities and specificities to the starting non-human antibody. (see PCT WO 93/06213 published Apr. 1, 1993). Unlike traditional humanization of non-human antibodies by CDR grafting, this technique provides completely human antibodies, which have no FR or CDR residues of non-human origin.

In one embodiment, an antibody is a "humanized" antibody. A humanized antibody is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. Humanized or other monoclonal antibodies can have additional conservative amino acid substitutions, which have substantially no effect on antigen binding or other immunoglobulin functions. Humanized antibodies can be constructed by means of genetic engineering (see for example, U.S. Pat. No. 5,585,089).

In particular embodiments, an anti-$\beta^{AT87Q}$-globin antigen binding fragment thereof, is formatted as a Camel Ig, a Llama Ig, an Alpaca Ig, Ig NAR, a Fab' fragment, a F(ab')$_2$ fragment, a bispecific Fab dimer (Fab2), a trispecific Fab trimer (Fab3), an Fv, an single chain Fv protein ("scFv"), a bis-scFv, (scFv)$_2$, a minibody, a diabody, a triabody, a tetrabody, a disulfide stabilized Fv protein ("dsFv"), and a single-domain antibody (sdAb, a camelid VHH, Nanobody).

"Camel Ig" or "camelid VHH" as used herein refers to the smallest known antigen-binding unit of a heavy chain antibody (Koch-Nolte, et al, FASEB J., 21: 3490-3498 (2007)). A "heavy chain antibody" or a "camelid antibody" refers to an antibody that contains two VH domains and no light chains (Riechmann L. et al, J. Immunol. Methods 231:25-38 (1999); WO94/04678; WO94/25591; U.S. Pat. No. 6,005,079).

"IgNAR" of "immunoglobulin new antigen receptor" refers to class of antibodies from the shark immune repertoire that consist of homodimers of one variable new antigen receptor (VNAR) domain and five constant new antigen receptor (CNAR) domains. IgNARs represent some of the smallest known immunoglobulin-based protein scaffolds and are highly stable and possess efficient binding characteristics. The inherent stability can be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulphide bridges, and patterns of intra-loop hydrogen bonds.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs) of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *PNAS USA* 90: 6444-6448 (1993). Triabodies and tetrabodies are also described in Hudson et al., *Nat. Med.* 9:129-134 (2003).

"Single domain antibody" or "sdAb" or "nanobody" refers to an antibody fragment that consists of the variable region of an antibody heavy chain (VH domain) or the variable region of an antibody light chain (VL domain) (Holt, L., et al, *Trends in Biotechnology*, 21(11): 484-490).

"Single-chain Fv" or "scFv" antibody fragments comprise the VH and VL domains of antibody, wherein these domains are present in a single polypeptide chain and in either orientation (e.g., VL-VH or VH-VL). Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

In preferred embodiments, the anti-βS-globin antigen binding fragment is an scFv. In particular embodiments, the scFv is a murine, human or humanized scFv. Single chain antibodies may be cloned form the V region genes of a hybridoma specific for a desired target. The production of such hybridomas has become routine. A technique which can be used for cloning the variable region heavy chain (VH) and variable region light chain (VL) has been described, for example, in Orlandi et al., *PNAS,* 1989; 86: 3833-3837.

In various embodiments, an anti-βS-globin antibody or antigen binding fragment thereof comprises a variable light chain sequence comprising CDRL1-CDRL3 sequences set forth in SEQ ID NOs: 1-3, and/or a variable heavy chain sequence comprising CDRH1-CDRH3 sequences set forth in SEQ ID NOs: 4-6. In some embodiments, the anti-ROR1 antibody or antigen binding fragment thereof comprises a variable light chain sequence as set forth in SEQ ID NO: 7 and/or a variable heavy chain sequence as set forth in SEQ ID NO: 8.

An exemplary $\beta^S$-globin-specific binding domain is an immunoglobulin variable region specific for $\beta^S$-globin that comprises at least one human framework region. A "human framework region" refers to a wild type (i.e., naturally occurring) framework region of a human immunoglobulin variable region, an altered framework region of a human immunoglobulin variable region with less than about 50% (e.g., preferably less than about 45%, 40%, 30%, 25%, 20%, 15%, 10%, 5%, or 1%) of the amino acids in the region are deleted or substituted (e.g., with one or more amino acid residues of a nonhuman immunoglobulin framework region at corresponding positions), or an altered framework region of a nonhuman immunoglobulin variable region with less than about 50% (e.g., less than 45%, 40%, 30%, 25%, 20%, 15%, 10%, or 5%) of the amino acids in the region deleted or substituted (e.g., at positions of exposed residues and/or with one or more amino acid residues of a human immunoglobulin framework region at corresponding positions) so that, in one aspect, immunogenicity is reduced.

In certain embodiments, a human framework region is a wild type framework region of a human immunoglobulin variable region. In certain other embodiments, a human framework region is an altered framework region of a human immunoglobulin variable region with amino acid deletions or substitutions at one, two, three, four, five, six, seven, eight, nine, ten or more positions. In other embodiments, a human framework region is an altered framework region of a non-human immunoglobulin variable region with amino acid deletions or substitutions at one, two, three, four, five, six, seven, eight, nine, ten or more positions.

$\beta^{AT87Q}$-globin-specific binding domains provided in particular embodiments also comprise one, two, three, four, five, or six CDRs. Such CDRs may be nonhuman CDRs or altered nonhuman CDRs selected from CDRL1, CDRL2 and CDRL3 of the light chain and CDRH1, CDRH2 and CDRH3 of the heavy chain. In certain embodiments, a $\beta^{AT87Q}$-globin-specific binding domain comprises (a) a light chain variable region that comprises a light chain CDRL1, a light chain CDRL2, and a light chain CDRL3, and (b) a heavy chain variable region that comprises a heavy chain CDRH1, a heavy chain CDRH2, and a heavy chain CDRH3.

In one embodiment, a $\beta^S$-globin-specific binding domain comprises light chain CDR sequences set forth in SEQ ID NOs: 1-3. In a particular embodiment, a $\beta^S$-globin-specific binding domain comprises light chain CDR sequences with at least 85%, 86%, 87%, 88%, 89%, 90%, 91%, 92%, 93%, 94%, 95%, 96%, 97%, 98%, or 99% amino acid identity to the light chain CDR sequences set forth in SEQ ID NOs: 1-3.

In one embodiment, a $\beta^S$-globin-specific binding domain comprises heavy chain CDR sequences set forth in SEQ ID NOs: 4-6. In a particular embodiment, a $\beta^S$-globin-specific binding domain comprises heavy chain CDR sequences with at least 85%, 86%, 87%, 88%, 89%, 90%, 91%, 92%, 93%, 94%, 95%, 96%, 97%, 98%, or 99% amino acid identity to the heavy chain CDR sequences set forth in SEQ ID NOs: 4-6.

In particular embodiments, the anti-$\beta^S$-globin antibody or antigen binding fragment thereof comprises one or more light chain CDRs as set forth in any one of SEQ ID NOs: 1-3 and/or one or more heavy chain CDRs as set forth in any one of SEQ ID NOs: 4-6. In certain embodiments, the anti-$\beta^S$-globin antibody or antigen binding fragment thereof comprises a variable light chain sequence as set forth in SEQ ID NO: 7 and/or a variable heavy chain sequence as set forth in SEQ ID NO: 8.

In particular embodiments, the anti-$\beta^S$-globin antibody or antigen binding fragment thereof comprises one or more light chain CDRs as set forth in any one of SEQ ID NOs: 1-3 and/or one or more heavy chain CDRs as set forth in any one of SEQ ID NOs: 4-6. In certain embodiments, the anti-$\beta^S$-globin antibody or antigen binding fragment thereof comprises a variable light chain sequence with at least 85%, 86%, 87%, 88%, 89%, 90%, 91%, 92%, 93%, 94%, 95%, 96%, 97%, 98%, or 99% amino acid identity to the variable light chain sequence set forth in SEQ ID NO: 7 and/or a variable heavy chain sequence with at least 85%, 86%, 87%, 88%, 89%, 90%, 91%, 92%, 93%, 94%, 95%, 96%, 97%, 98%, or 99% amino acid identity to the variable heavy chain sequence set forth in SEQ ID NO: 8.

D. Conjugates

In various embodiments, a conjugate comprising an anti-$\beta^S$-globin antibody or antigen binding fragment thereof and a label is provided. In preferred embodiments, a conjugate comprises an anti-$\beta^S$-globin antibody or antigen binding fragment thereof, and a detectable label or a label capable of producing a detectable signal. In more preferred embodiments, a conjugate comprises an anti-$\beta^S$-globin antibody or antigen binding fragment thereof, coupled to a detectable label. In even more preferred embodiments, a conjugate comprises an anti-$\beta^S$-globin antibody or antigen binding fragment thereof, covalently bound, or chemically coupled to, a detectable label.

As used herein, the term "label" refers to a detectable label or a label capable of producing a detectable signal. In particular embodiments, a label comprises a radionuclides, nucleic acid, small molecule, or polypeptide. In some embodiments, labels are directly detectable. In some embodiments, labels are indirectly detectable.

Illustrative examples of detectable labels suitable for use in conjugates contemplated in particular embodiments include, but are not limited to: haptens, fluorescent molecules, fluorescent dyes, fluorescent proteins, chromophores, metal ions, gold particles, silver particles, magnetic particles, radionuclides, polypeptides, enzymes, luminescent compounds, or oligonucleotides.

Illustrative examples of molecules suitable for use as detectable labels in particular embodiments include, but are not limited to: Oregon Green®; Pacific Blue™; Pacific Orange™; Pacific Green™; Cascade Blue™; Cascade Yellow™; Lucifer Yellow™; Marina Blue™; Texas Red® (TxRed); AlexaFluor®(AF) dyes, e.g., AF350, AF405, AF488, AF500, AF514, AF532, AF546, AF555, AF568, AF594, AF610, AF633, AF635, AF647, AF680, AF700, AF710, AF750, AF790, and AF800; QDot® nanocrystals, e.g., Qdot®525, Qdot®565, Qdot®585, Qdot®605, Qdot®655, Qdot®705, and Qdot®800; DyLight™ Dyes (DL), e.g., DL549, DL649, DL680, and DL800; fluorescein or a derivative thereof, e.g., fluorescein isothiocyanate, carboxyfluorescein, and dichlorotriazinylamine fluorescein; digoxigenin; dinitrophenol (DNP); trinitrophenol (TNP); biotin; Cy dyes, e.g., Cy2, Cy3, Cy3.5, Cy5, Cy5.5, Cy7, and Cy 7.5; Phycoerythrin (PE, R-Phycoerythrin (RPE)); B-Phycoerythrin (BPE); Peridinin Chlorophyll (PerCP); Allophycocyanin (APC); C-Phycocyanin; Atto® Dyes, e.g., Atto 390, Atto 425, Atto 465, Atto 488, Atto 495, Atto 514Atto 520, Atto 532, Atto 550, Atto 565, Atto 590, Atto 594, Atto 610, Atto 620, Atto 633, Atto 647, Atto 655, Atto 665, Atto 680, Atto 700, Atto 725, and Atto 740; Super Bright™ Dyes, e.g., Super Bright™ 436, Super Bright™ 600, Super Bright™ 645, Super Bright™ 702, and Super Bright™ 780; Brilliant™ Dyes, e.g., Brilliant™ Violet 421, Brilliant™ Violet 480, Brilliant™ Violet 510, Brilliant™ Violet 605, Brilliant Violet™ 650, Brilliant Violet™ 711, Brilliant Violet™ 786, Brilliant™ Ultraviolet 395 (BUV395), Brilliant™ Ultraviolet 496 (BUV496), Brilliant™ Ultraviolet 563 (BUV563), Brilliant™ Ultraviolet 661 (BUV661), Brilliant™ Ultraviolet 737 (BUV737), Brilliant™ Ultraviolet 805 (BUV805), Brilliant™ Blue 515 (BB515), and Brilliant™ Blue 700 (BB700); and IR Dyes, e.g., IR Dye 680, IR Dye 680LT, IR Dye 700, IR Dye 700DX, IR Dye 800, IR Dye 800RS, and IR Dye 800CW.

Illustrative examples of tandem fluorescent dye molecules suitable for use as detectable labels include, but are not limited to: RPE-Cy5, RPE-Cy5.5, RPE-Cy7, RPE-CF594, RPE-AlexaFluor® tandem conjugates; RPE-Alexa610, RPE-TxRed, APC-H7, APC-R700, APC-Alexa600, APC-Alexa610, APC-Alexa750, APC-Cy5, APC-Cy5.5, and APC-Cy7.

Illustrative examples of fluorescent proteins suitable for use as detectable labels include, but are not limited to: GFP, eGFP, BFP, CFP, YFP, DsRed, DsRed2, mRFP, mBanana, mOrange, dTomato, tdTomato, mTangerine, mStrawberry, mCherry, mPlum, and mRaspberry.

Illustrative examples of enzymes suitable for use as detectable labels include, but are not limited to: alkaline phosphatase, horseradish peroxidase, luciferase, and β-galactosidase.

Illustrative examples of radionuclides suitable for use as detectable labels include, but are not limited to: carbon (14C), chromium (51Cr), cobalt (57Co), fluorine (18F), gadolinium (153Gd, 159Gd), germanium (68Ge), holmium (166Ho), indium (115In, 113In, 112In, mIn), iodine (125I, 123I, 121I), lanthanium (140La), lutetium (177Lu), manganese (54Mn), molybdenum (99 Mo), palladium (103 Pd), phosphorous (32 P), praseodymium (142 Pr), promethium (149Pm), rhenium (186Re, 188Re), rhodium (105Rh), rutheroium (97Ru), samarium (153Sm), scandium (47Sc), selenium (75Se), (85Sr), sulphur (35S), technetium (99Tc), thallium (201Ti), tin (113Sn, 117Sn), tritium (3H), xenon (133Xe), ytterbium (169Yb, 175Yb), and yttrium (90Y).

In particular embodiments, a conjugate comprises an antibody or antibody fragment that is conjugated, coupled, or linked (e.g., covalently bonded) to one or more labels. In certain embodiments, a label may be conjugated, coupled, or linked to an antibody or fragment either directly or indirectly (e.g., via a linker group). An antibody can be directly covalently bound to one or more labels when the antibody and the label each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

In particular embodiments, it may be desirable to couple, conjugate, or link an antibody or antibody fragment to one or more labels via a monovalent or polyvalent linker or a spacer. A linker or spacer can be used to provide sufficient distance between an antibody and a label to avoid steric hindrance or interference with antibody binding capabilities. It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

In certain embodiments, a linker has an overall chain length of about 1-100 atoms, 1-80 atoms, 1-60 atoms, 1-40 atoms, 1-30 atoms, 1-20 atoms, or 1, 2, 3, 4, 5, 6, 7, 8, 9, 10, 11, 12, 13, 14, 15, 16, 17, 18, 19, or 20 atoms, wherein the atoms in the chain comprise C, S, N, P, and O.

Illustrative examples of linkers or linkages useful in particular embodiments of the present invention include, but are not limited to one or more of the following: —C(O)—, —NH—C(O)—, —C(O)—NH—, —C(O)—NH—(CH$_2$)$_{2-6}$—NH—C(O)—, —NH—(CH$_2$)$_{2-6}$—NH—C(O)—, -triazole-, —(CH$_2$)$_{2-6}$—NH—C(O)—, —S—(CH$_2$)$_{2-6}$—NH—C(O)—, —S—(CH$_2$)$_{0-6}$—CH(CONH$_2$)—(CH$_2$)$_{0-6}$—NH—C(O)—, —S—(CH$_2$)$_{0-6}$—CH(CONH-PEG)-(CH$_2$)$_{0-6}$—NH—C(O)—, —S—S—(CH$_2$)$_{2-6}$—NH—C(O)—, —S—S—(CH$_2$)$_{0-6}$—CH(CONH$_2$)—(CH$_2$)$_{0-6}$—NH—C(O)—, —S—S—(CH$_2$)$_{0-6}$—CH(CONH-PEG)-(CH$_2$)$_{0-6}$—NH—C(O)—, —NH—(CH$_2$)$_{0-6}$—CH(CONH-PEG)-(CH$_2$)$_{0-6}$—NH—C(O)—, —NH—(CH$_2$)$_{0-6}$—CH(CONH$_2$)—(CH$_2$)$_{0-6}$—NH—C(O)— —C=N—O—(CH$_2$)$_{2-6}$—NH—C(O)—, —C=N—NH—(CO)—(CH$_2$)$_{2-6}$—NH—C(O)—, -succinimide-, —(CH$_2$)$_{2-6}$—NH—C(O)—, -diazodicarboxamide-(Phenyl)-J-(CH$_2$)$_{2-6}$—NH—C(O)—, J is O, CH$_2$, NH, S, NH(CO), (CO)NH, —NH—(CH$_2$)$_{2-6}$—, (CH$_2$)$_{1-6}$—NH—C(O)—NH—(CH$_2$)$_{2-6}$—, —C(S)—(CH$_2$)$_{0-6}$—, —(CH$_2$)$_{1-6}$—C(O)—NH—(CH$_2$)$_{2-6}$—, —(CH$_2$)$_{1-6}$—NH—C(O)—(CH$_2$)$_{2-6}$—, —(CH$_2$)$_{1-6}$—O—C(O)—NH—(CH$_2$)$_{2-6}$—, —(CH$_2$)$_{1-6}$—NH—C(O)—O—(CH$_2$)$_{2-6}$—, (CH$_2$)$_{1-6}$—NH—(CH$_2$)$_{2-6}$, (CH$_2$)$_{1-6}$—C(O—(CH$_2$)$_{2-6}$—, branched or unbranched-C1-C16-alkyl, branched or unbranched-C1-C16-alkyl where one of the carbon atoms can be optionally substituted with a heteroatom, R$^2$—NH—(CH$_2$)$_{2-6}$—NH—C(O)—, R$^2$—S—(CH$_2$)$_{2-6}$—NH—C(O)—, R$^2$-triazole-(CH$_2$)$_{2-6}$—NH—C(O)—, R$^2$—NH—O—(CH$_2$)$_{2-6}$—NH—C(O)—, R$^2$=N—NH—(CO)—(CH$_2$)$_{2-6}$—NH—C(O)—, R$^2$ is one to three bifunctional or trifunctional substituted cross-linking organic radicals selected from the group consisting of alkyl, substituted alkyl, cycloalkyl, aryl, heteroaryl, polyethylene glycol (PEG) [i.e., —(CH$_2$CH$_2$O)$_{1-20}$].

In particular embodiments, a conjugate comprises an anti-β$^S$-globin antibody or antibody fragment covalently bound to a polypeptide-based label, e.g., a fluorescent protein or enzyme, via a polypeptide linker contemplated elsewhere herein, infra.

E. Polypeptides

Various polypeptides are contemplated herein, including, but not limited to antibodies and antigen binding fragments thereof.

"Polypeptide," "polypeptide fragment," "peptide" and "protein" are used interchangeably, unless specified to the contrary, and according to conventional meaning, i.e., as a sequence of amino acids. Polypeptides are not limited to a specific length, e.g., they may comprise a full-length protein sequence or a fragment of a full-length protein, and may include post-translational modifications of the polypeptide, for example, glycosylations, acetylations, phosphorylations and the like, as well as other modifications known in the art, both naturally occurring and non-naturally occurring.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. In particular embodiments, an isolated polypeptide is a synthetic polypeptide, a semi-synthetic polypeptide, or a polypeptide obtained or derived from a recombinant source.

Similarly, an "isolated cell" refers to a cell that has been obtained from an in vivo tissue or organ and is substantially free of extracellular matrix.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of an anti-β$^S$-globin antibody or antigen binding fragment thereof by introducing one or more amino acid substitutions, deletions, additions and/or insertions. In particular embodiments, polypeptides include polypeptides having at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% amino acid identity to any of the reference sequences contemplated herein, typically where the variant maintains at least one biological activity of the reference sequence. In particular embodiments, the biological activity is binding affinity.

Polypeptides variants include biologically active "polypeptide fragments." Illustrative examples of biologically active polypeptide fragments include binding domains and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of an anti-β$^S$-globin antibody, useful fragments include, but are not limited to: a CDR region, a CDR3 region of the heavy or light chain; a variable region of a heavy or light chain; a portion of an antibody chain or variable region including two CDRs; and the like.

The polypeptide may also be fused in-frame or conjugated to a linker or other sequence for ease of synthesis, purification or identification of the polypeptide (e.g., poly-His), or to enhance binding of the polypeptide to a solid support.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., (*Molecular Biology of the Gene,* Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (Natl. Biomed. Res. Found., Washington, D.C.).

In certain embodiments, a polypeptide variant comprises one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acids | One letter code | Three letter code | Codons | | | | | |
|---|---|---|---|---|---|---|---|---|
| Alanine | A | Ala | GCA | GCC | GCG | GCU | | |
| Cysteine | C | Cys | UGC | UGU | | | | |
| Aspartic acid | D | Asp | GAC | GAU | | | | |
| Glutamic acid | E | Glu | GAA | GAG | | | | |
| Phenylalanine | F | Phe | UUC | UUU | | | | |
| Glycine | G | Gly | GGA | GGC | GGG | GGU | | |
| Histidine | H | His | CAC | CAU | | | | |
| Isoleucine | I | Iso | AUA | AUC | AUU | | | |
| Lysine | K | Lys | AAA | AAG | | | | |
| Leucine | L | Leu | UUA | UUG | CUA | CUC | CUG | CUU |
| Methionine | M | Met | AUG | | | | | |
| Asparagine | N | Asn | AAC | AAU | | | | |
| Proline | P | Pro | CCA | CCC | CCG | CCU | | |
| Glutamine | Q | Gln | CAA | CAG | | | | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | ACU | | |
| Valine | V | Val | GUA | GUC | GUG | GUU | | |
| Tryptophan | W | Trp | UGG | | | | | |
| Tyrosine | Y | Tyr | UAC | UAU | | | | |

Guidance in determining which amino acid residues can be substituted, inserted, or deleted without abolishing biological activity can be found using computer programs well known in the art, such as DNASTAR, DNA Strider, Geneious, MacVector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. Co., p. 224).

In making such changes, the hydropathic index of amino acids may be considered. The importance of the hydropathic amino acid index in conferring interactive biologic function on a protein is generally understood in the art (Kyte and Doolittle, 1982, incorporated herein by reference). Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

Polypeptide variants further include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

Polypeptides contemplated in particular embodiments include fusion polypeptides. In preferred embodiments, fusion polypeptides and polynucleotides encoding fusion polypeptides are provided, e.g., light chain or heavy chain variable regions linked by a linker sequence.

Fusion polypeptides may optionally comprise a linker that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary linkers include, but are not limited to the following amino acid sequences: glycine polymers $(G)_n$; glycine-serine polymers $(G_{1-5}S_{1-5})_n$, where n is an integer of at least one, two, three, four, or five; glycine-alanine polymers; alanine-serine polymers; GGG (SEQ ID NO: 10); DGGGS (SEQ ID NO: 11); TGEKP (SEQ ID NO: 12) (see e.g., Liu et al., *PNAS* 5525-5530 (1997)); GGRR (SEQ ID NO: 13) (Pomerantz et al. 1995, supra); $(GGGGS)_n$ (SEQ ID NO: 14) (Kim et al., *PNAS* 93, 1156-1160 (1996).); EGKSSGSGSESKVD (SEQ ID NO: 15) (Chaudhary et al., 1990, *Proc. Natl. Acad. Sci. U.S.A.* 87:1066-1070); KESGSVSSEQLAQFRSLD (SEQ ID NO: 16) (Bird et al., 1988, *Science* 242:423-426), GGRRGGGS (SEQ ID NO: 17); LRQRDGERP (SEQ ID NO: 18); LRQKDGGGSERP (SEQ ID NO: 19); LRQKD(GGGS)$_2$ERP (SEQ ID NO: 20). Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods.

Fusion polypeptides are typically linked C-terminus to N-terminus, although they can also be linked C-terminus to C-terminus, N-terminus to N-terminus, or N-terminus to C-terminus. The polypeptides of the fusion protein can be in any order or a specified order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as discussed elsewhere herein.

In one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments or to facilitate transport of the fusion protein through the cell membrane.

Fusion polypeptides may further comprise a polypeptide cleavage signal between each of the polypeptide domains described herein. In addition, a polypeptide cleavage site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic*, 5(8); 616-26).

F. Polynucleotides

In preferred embodiments, a polynucleotide encoding an antibody or antigen binding fragment thereof contemplated herein is provided. As used herein, the terms "polynucleotide" or "nucleic acid" refers to messenger RNA (mRNA), RNA, genomic DNA (gDNA), complementary DNA (cDNA) or recombinant DNA. Polynucleotides include single and double stranded polynucleotides. In particular embodiments, polynucleotides include polynucleotides or variants having at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences contemplated herein. In various illustrative embodiments, polynucleotides encoding a polypeptide contemplated herein, including, but not limited to the polypeptide sequences set forth in SEQ ID NOs: 1-20.

In particular embodiments, polynucleotides are provided that encode at least about 5, 10, 25, 50, 100, 150, 200, 250, 300, 350, 400, 500, 1000, 1250, 1500, 1750, or 2000 or more contiguous amino acid residues of a polypeptide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., Current Protocols in Molecular Biology, John Wiley & Sons Inc, 1994-1998, Chapter 15.

As used herein, "isolated polynucleotide" refers to a polynucleotide that has been purified from the sequences which flank it in a naturally-occurring state, e.g., a DNA fragment that has been removed from the sequences that are normally adjacent to the fragment. An "isolated polynucleotide" also refers to a complementary DNA (cDNA), a recombinant DNA, or other polynucleotide that does not exist in nature and that has been made by the hand of man.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the premessenger (premRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

Moreover, it will be appreciated by those of ordinary skill in the art that, as a result of the degeneracy of the genetic code, there are many nucleotide sequences that encode a polypeptide, or fragment of variant thereof, as described herein. Some of these polynucleotides bear minimal homology to the nucleotide sequence of any native sequence. Nonetheless, polynucleotides that vary due to differences in codon usage are specifically contemplated in particular embodiments, for example polynucleotides that are optimized for human and/or primate codon selection.

Polynucleotides can be prepared, manipulated and/or expressed using any of a variety of well-established techniques known and available in the art. In order to express a desired polypeptide, a nucleotide sequence encoding the polypeptide, can be inserted into appropriate vector.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Validation Assays

HbS Staining and FACS Analysis

For HbS staining, 10 µL of whole blood was washed with 1 mL of PBS containing 0.1% HSA three times and fixed in 300 µL PBS containing 0.05% glutaraldehyde for 10 min at room temperature. 600 µL of PBS containing 0.1% HSA was added to the washed cells and the cells were centrifuged at 400× g for 5 min. The supernatant was removed and the cell pellet was washed twice with 1 mL of PBS containing 0.1% HSA. The cell pellet was re-suspended in 300 µL PBS containing 0.1% Triton X-100, and incubated for 4 min at room temperature. 600 µL of PBS containing 0.1% HSA was added to the resuspended cells and the cells were centrifuged 400× g for 5 min. The supernatant was removed and the cells were re-suspended cells in 300 µL of PBS containing 0.1% HSA.

10 µL cell suspension was combined with 30 µL of FACS buffer (PBS, 2% FBS) and 10 µL anti-HbS antibody. The mixture was incubated at room temperature for 30 min. 1 mL of FACS buffer was added to the mixture and centrifuged at 400× g for 5 min. The supernatant was removed and the cell pellet was washed with 1 mL FACS buffer and centrifuged at 400× g for 5 min. The supernatant was removed and the cell pellet was re-suspended in 10 µL of FACS buffer.

10 µL of cell suspension was combined with 40 µL of FACS buffer and 1 µL secondary antibody. The mixture was incubated at room temperature for 15 min, with protection from light. 1 mL of FACS buffer was added to the mixture and centrifuge at 400× g for 5 min. The supernatant was removed and the cell pellet was re-suspended in 300 µL of FACS buffer and analyzed using a flow cytometer.

LVV Transduction and Vector Copy Number (VCN)

Human $CD34^+$ cells were re-suspended in pre-stimulation medium (SCGM (Stem Cell Growth Medium), 100 ng/mL hSCF, 100 ng/mL hTPO and 100 ng/mL Flt3-L) at a cell density of $1×10^6$ cells/mL for 48 h. The cultured cells were transduced with lentiviral vector (LVV). For each 100 µL sample, $4×10^5$ $hCD34^+$ cells in SCGM were combined with 40 µL of LVV and 10 µL of 10× cytokines in a 96 well flat bottom plate. The $hCD34^+$ cells were transduced at 37° C., 5% $CO_2$ incubator for 24±2 hours.

The transduced $hCD34^+$ cells were washed with SCGM and re-suspended in 2 mL SCGM with SCF, TPO, Flt3-L, and IL-3, and transferred to a standard 12-well non-adherent tissue culture plate. Cells were maintained for an additional 6 days in a standard humidified tissue culture incubator (5% CO2) and then subjected to vector copy number (VCN) analysis using qPCR. The qPCR was performed using primers and probes specific to both the vector and an endogenous control gene. VCN was determined by dividing the amount of vector signal by the amount of the endogenous control gene.

HSC In Vitro Erythroid Differentiation

After LVV transduction for 24 h, cells were washed and resuspended in appropriate amount of HF Expansion Media (IMDM, 1% Pen/Strep, 20 ng/mL hSCF, 1 ng/mL hIL-3, 2 IU/mL EPO, 20% heat-inactivated FBS) to a cell density of $\sim5.0×10^5$ cells/mL and plated on non-tissue culture treated plates. Cells were cultured in HF Expansion Media for 7 days and checked every 2-3 days to keep density below $1.0×10^6$ cells/mL. After 7 days in culture, cells were centrifuged at 300× g for 5 minutes at room temperature and resuspended in HF Differentiation Media (IMDM, 1% Pen/Strep, 2 IU/mL EPO, 20% heat-inactivated FBS, 200 ug/mL apo-transferrin) at a density of $3.0-5.0×10^5$ cells/mL. Cells were plated on non-tissue culture treated plates and cultured in HF Differentiation Media for 7 days. Culture density was maintained at $5.0×10^5$ cells/mL. After 7 days of culture, cells were monitored for CD235a (GPA) expression. HbS percentage was determined by flow analysis after 4-7 more days of culture.

Example 2

HbS Staining of Normal and Sickle Red Blood Cells

Normal and sickle patient whole blood were fixed, permeabilized, and mixed together. The cells were stained with HbS antibody (Clone 15H4.D9.G5) for approximately 30 minutes at room temperature. Following incubation, cells were washed and stained with APC conjugated anti-mouse secondary antibody (Abcam # Ab130782) for 15 mins at room temperature. A/A (normal hemoglobin; HbA) and S/S (sickle hemoglobin; HbS) red blood cells were separated, manifested by two peaks. Increasing the voltage of APC channel in the flow cytometer did not further separate the two peaks. These results indicate that HbS antibody is specific to S-hemoglobin, but not A-hemoglobin. FIG. 1.

Example 3

Titration of HbS Antibody to Detect the Sickle Red Blood Cells

Figure 2:
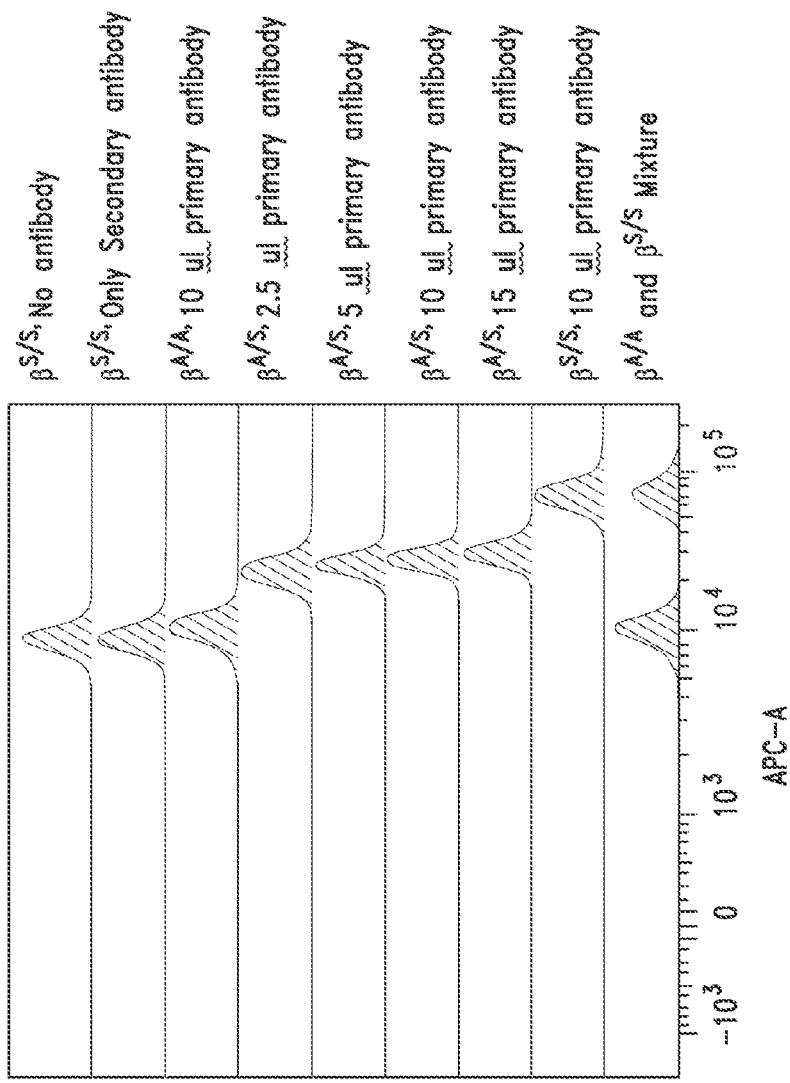
FIG. 2 shows HbS staining of blood from patients with normal hemoglobin (A/A), sickle trait (A/S), and sickle hemoglobin (S/S) with an anti-$\beta^S$ antibody.

Whole blood from patients with normal hemoglobin (A/A), sickle trait (A/S), and sickle hemoglobin (S/S) was fixed and permeabilized. The cells were stained with HbS antibody as described in Example 2. The A/S peak was between the A/A peak and the S/S peak. In addition, the A/S red blood cells were stained with different concentration of HbS antibody (2.5 µL, 5 µL, 10 µL and 15 µL). The A/S peak did not show significant shift with different HbS amount, as low as 2.5 µL HbS antibody is enough for HbS staining per sample. FIG. 2.

Example 4

HbS Staining Can Determine the Percentage of S-Hemoglobin Positive Cells

Figure 3:
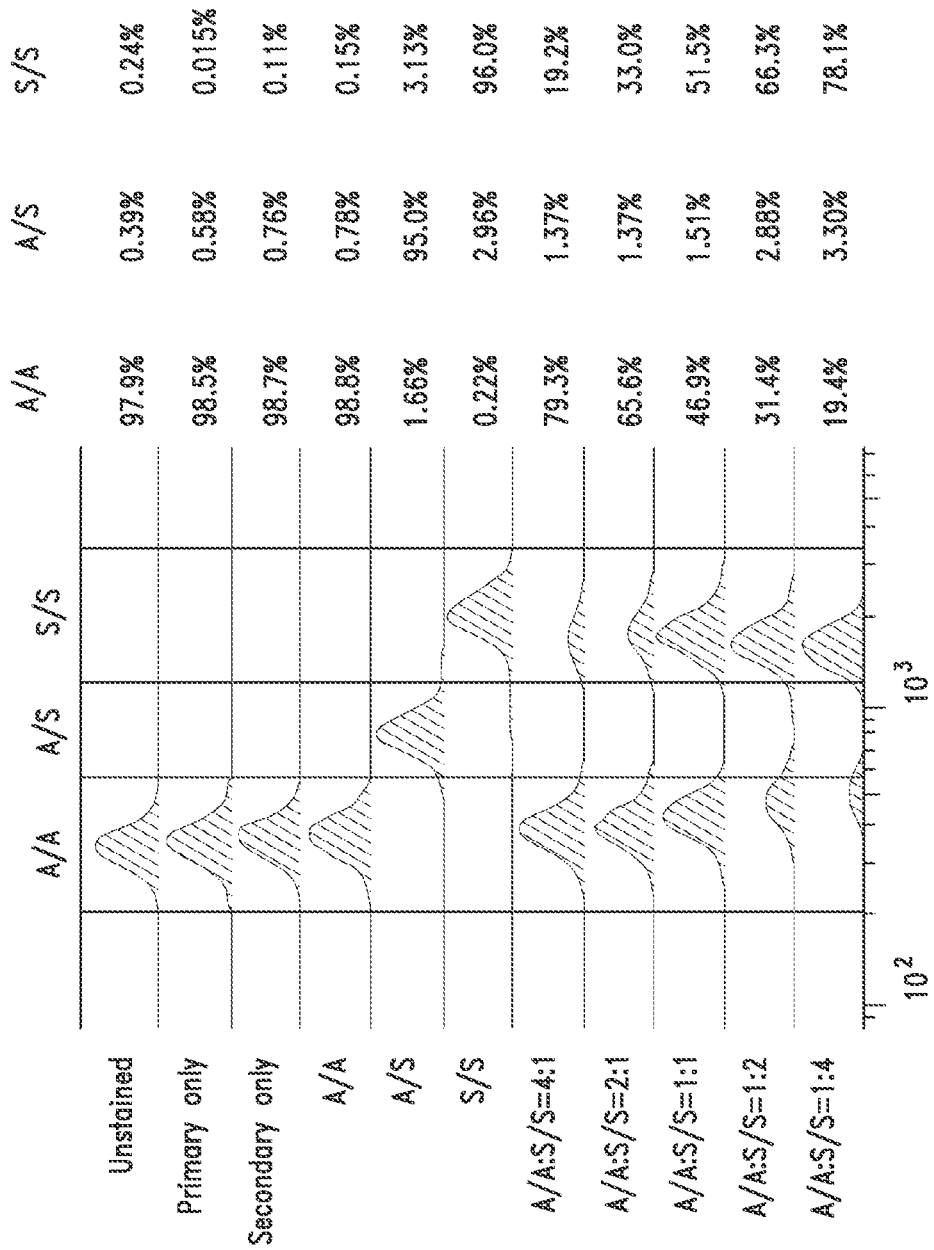
FIG. 3 shows percentage of red blood cells from patients with normal hemoglobin (A/A), sickle trait (A/S), and sickle hemoglobin (S/S) stained with an anti-$\beta^S$ antibody.

Normal (A/A) and sickle patient (S/S) whole blood were fixed, permeabilized and mixed at different ratios (4:1, 2:1, 1:1, 1:2 and 1:4). The cells were stained with HbS antibody as described in Example 2. The percentage of S-hemoglobin positive cells were determined by flow analysis. The amount of HbS detected increased as the ratio of HbA:HbS decreased. FIG. 3.

Example 5

Figure 4:
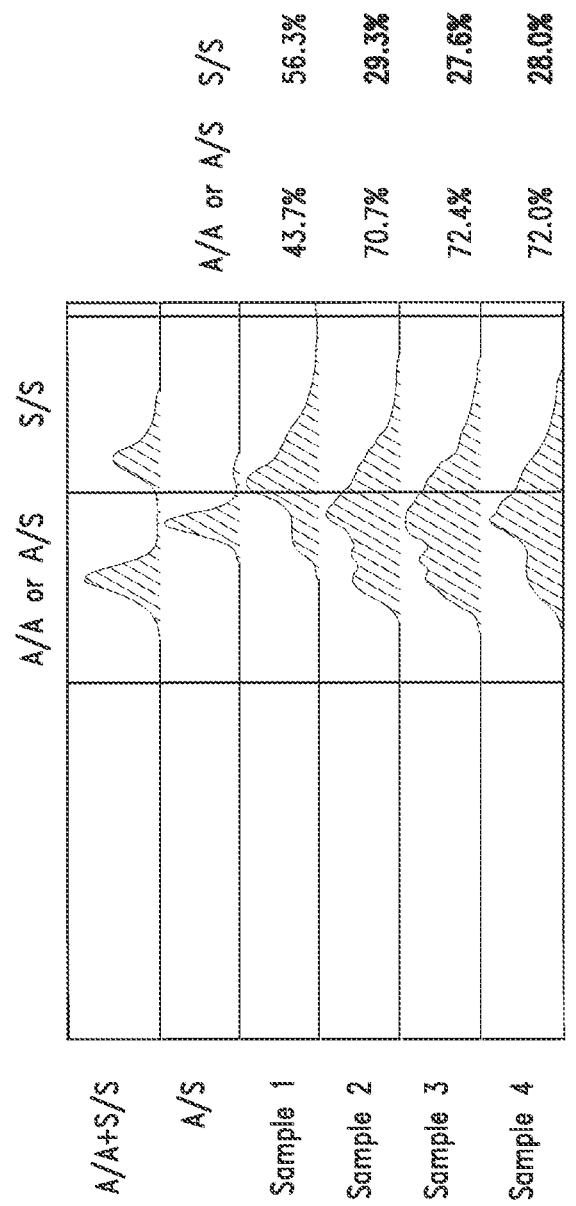
FIG. 4 shows percentage of red blood cells from patients with normal hemoglobin (A/A), sickle trait (A/S), and sickle hemoglobin (S/S) stained with an anti-$\beta^S$ antibody. The red blood cells were obtained from bone-marrow enriched CD34+ cells transduced with a lentiviral vector encoding an anti-sickling β-globin and subjected to erythroid differentiation.

Sickle (S/S) Bone Marrow Cells Show Reduced HbS Expression After Transduction with Lentiviral Vector Encoding an Anti-Sickling β-Globin $CD34^+$ cells were enriched were enriched from sickle patient (S/S) bone marrow. The cells were pre-stimulated and were mock-transduced (sample 1) or transduced with a lentiviral vector (LVV) encoding an anti-sickling β-globin (samples 2-4). Cells were subjected to in vitro erythroid differentiation for 14 days, then stained with HbS antibody as described in Example 2. Cells transduced with LVV encoding an anti-sickling β-globin showed decreased HbS expression compared to mock-transduced cells, from 56.3% to 28.0%. FIG. 4.

Example 6

Figure 5:
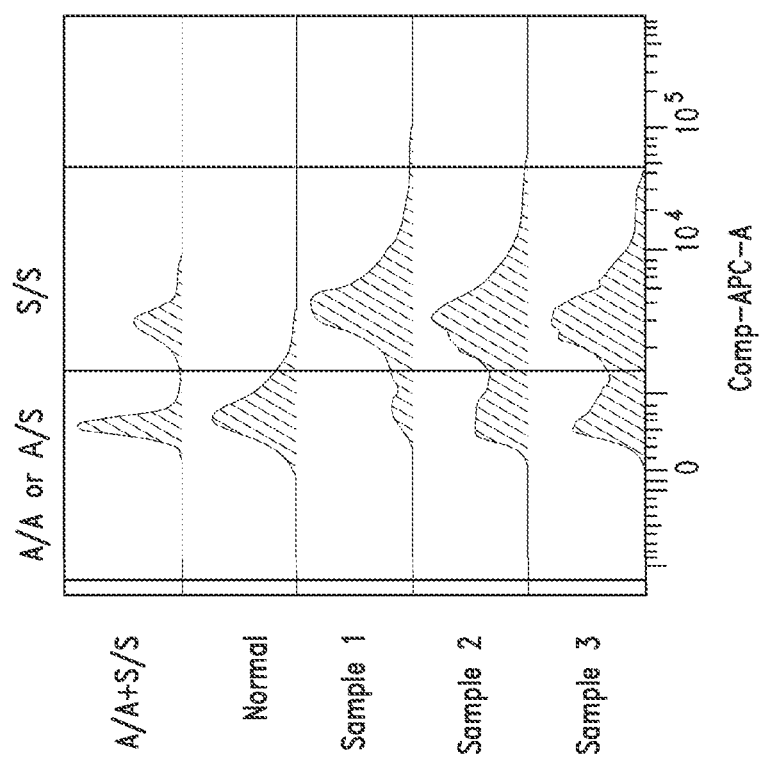
FIG. 5 shows percentage of red blood cells from patients with normal hemoglobin (A/A), sickle trait (A/S), and sickle hemoglobin (S/S) stained with an anti-$\beta^S$ antibody. The red blood cells were obtained from plerixafor mobilized peripheral blood, enriched for CD34+ cells and transduced with a lentiviral vector encoding an anti-sickling β-globin and subjected to erythroid differentiation.

Sickle (S/S) Mobilized Peripheral Blood Cells Show Reduced HbS Expression After Transduction with Lentiviral Vector Encoding an Anti-Sickling β-Globin Sickle patients were treated with Plerixafor to mobilized peripheral blood cells. The mobilized peripheral blood was enriched for $CD34^+$ cells. The $CD34^+$ cells were pre-stimulated with cytokines and mock-transduced (sample 1) or transduced with a lentiviral vector (LVV) encoding an anti-sickling β-globin (samples 2-3). Cells were subjected to in vitro erythroid differentiation for 14 days, then stained with HbS antibody as described in Example 2. Cells transduced with LVV encoding an anti-sickling β-globin showed decreased HbS expression compared to mock-transduced cells, from 83.0% to average 59.0%. FIG. 5.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An anti-$\beta^S$ globin antibody or antigen binding fragment thereof that binds a human βS globin polypeptide, wherein the anti-$\beta^S$ globin antibody or antigen binding fragment thereof comprises a variable light chain sequence as set forth in SEQ ID NO: 7 and a variable heavy chain sequence as set forth in SEQ ID NO: 8.

2. A conjugate, comprising the anti-$\beta^S$ globin antibody or antigen binding fragment thereof of claim 1; and a detectable label.

3. The conjugate of claim 2, wherein the detectable label is selected from the group consisting of: a hapten, a fluorescent dye, a fluorescent protein, a chromophore, a metal ion, a gold particle, a silver particle, a magnetic particle, a polypeptide, an enzyme, a luminescent compound, or an oligonucleotide.

4. A hybridoma comprising the anti-$\beta^S$ globin antibody of claim 1.

5. A polynucleotide encoding the anti-$\beta^S$ globin antibody or antigen binding fragment thereof of claim 1.

* * * * *

```
                        SEQUENCE LISTING

<160> NUMBER OF SEQ ID NOS: 24

<210> SEQ ID NO 1
<211> LENGTH: 16
<212> TYPE: PRT
<213> ORGANISM: Artificial Sequence
<220> FEATURE:
<223> OTHER INFORMATION: Made in Lab - Light chain CDR1

<400> SEQUENCE: 1

Lys Ser Ser Gln Ser Leu Leu Tyr Ser Asp Gly Lys Thr Tyr Leu Asn
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Made in Lab - Light chain CDR2

<400> SEQUENCE: 2

Leu Val Ser Lys Leu Asp Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Made in Lab - light chain CDR3

<400> SEQUENCE: 3

Trp Gln Gly Thr His Phe Pro Leu Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Made in Lab - heavy chain CDR1

<400> SEQUENCE: 4

Gly Asn Thr Phe Thr Asp Tyr Val Ile Ser
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Made in Lab - heavy chain CDR2

<400> SEQUENCE: 5

Glu Ile Tyr Leu Gly Ser Gly Ser Pro Lys Tyr Asn Glu Lys Phe Lys
1               5                   10                  15
Gly

<210> SEQ ID NO 6
<211> LENGTH: 5
```

```
<212> TYPE: PRT
<213> ORGANISM: Artificial Sequence
<220> FEATURE:
<223> OTHER INFORMATION: Made in Lab - heavy chain CDR3

<400> SEQUENCE: 6

Ile Gly Ala Gly Tyr
1               5

<210> SEQ ID NO 7
<211> LENGTH: 112
<212> TYPE: PRT
<213> ORGANISM: Artificial Sequence
<220> FEATURE:
<223> OTHER INFORMATION: Made in Lab - light chain variable region

<400> SEQUENCE: 7

Gly Ile Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Leu Thr Phe Gly Ala Gly Thr Lys Leu Glu Leu Lys
            100                 105                 110

<210> SEQ ID NO 8
<211> LENGTH: 114
<212> TYPE: PRT
<213> ORGANISM: Artificial Sequence
<220> FEATURE:
<223> OTHER INFORMATION: Made in Lab - heavy chain variable region

<400> SEQUENCE: 8

Glu Val Gln Leu Gln Glu Ser Gly Pro Glu Leu Val Lys Pro Gly Ala
1               5                   10                  15

Ser Val Lys Met Ser Cys Lys Ala Ser Gly Asn Thr Phe Thr Asp Tyr
            20                  25                  30

Val Ile Ser Trp Val Lys Gln Arg Thr Gly Gln Gly Leu Glu Trp Ile
        35                  40                  45

Gly Glu Ile Tyr Leu Gly Ser Gly Ser Pro Lys Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Lys Phe Ser Ser Leu Thr Phe Glu Asp Ser Ala Val Tyr Phe Cys
                85                  90                  95

Thr Arg Ile Gly Ala Gly Tyr Trp Gly Gln Gly Thr Thr Leu Thr Val
            100                 105                 110

Ser Ser

<210> SEQ ID NO 9
<211> LENGTH: 147
<212> TYPE: PRT
<213> ORGANISM: Homo sapiens
```

<400> SEQUENCE: 9

Met Val His Leu Thr Pro Val Glu Lys Ser Ala Val Thr Ala Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Thr Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145

<210> SEQ ID NO 10
<211> LENGTH: 3
<212> TYPE: PRT
<213> ORGANISM: Artificial Sequence
<220> FEATURE:
<223> OTHER INFORMATION: Exemplary linker sequence

<400> SEQUENCE: 10

Gly Gly Gly
1

<210> SEQ ID NO 11
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 11

Asp Gly Gly Gly Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 12

Thr Gly Glu Lys Pro
1               5

<210> SEQ ID NO 13
<211> LENGTH: 4
<212> TYPE: PRT
<213> ORGANISM: Artificial Sequence
<220> FEATURE:
<223> OTHER INFORMATION: Exemplary linker sequence

```
<400> SEQUENCE: 13

Gly Gly Arg Arg
1

<210> SEQ ID NO 14
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 14

Gly Gly Gly Gly Ser
1               5

<210> SEQ ID NO 15
<211> LENGTH: 14
<212> TYPE: PRT
<213> ORGANISM: Artificial Sequence
<220> FEATURE:
<223> OTHER INFORMATION: Exemplary linker sequence

<400> SEQUENCE: 15

Glu Gly Lys Ser Ser Gly Ser Gly Ser Glu Ser Lys Val Asp
1               5                   10

<210> SEQ ID NO 16
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 16

Lys Glu Ser Gly Ser Val Ser Ser Glu Gln Leu Ala Gln Phe Arg Ser
1               5                   10                  15

Leu Asp

<210> SEQ ID NO 17
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 17

Gly Gly Arg Arg Gly Gly Gly Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 18

Leu Arg Gln Arg Asp Gly Glu Arg Pro
1               5

<210> SEQ ID NO 19
<211> LENGTH: 12
<212> TYPE: PRT
<213> ORGANISM: Artificial Sequence
<220> FEATURE:
```

```
<223> OTHER INFORMATION: Exemplary linker sequence

<400> SEQUENCE: 19

Leu Arg Gln Lys Asp Gly Gly Gly Ser Glu Arg Pro
1               5                   10

<210> SEQ ID NO 20
<211> LENGTH: 16
<212> TYPE: PRT
<213> ORGANISM: Artificial Sequence
<220> FEATURE:
<223> OTHER INFORMATION: Exemplary linker sequence

<400> SEQUENCE: 20

Leu Arg Gln Lys Asp Gly Gly Gly Ser Gly Gly Gly Ser Glu Arg Pro
1               5                   10                  15

<210> SEQ ID NO 21
<211> LENGTH: 4
<212> TYPE: PRT
<213> ORGANISM: Artificial Sequence
<220> FEATURE:
<223> OTHER INFORMATION: Exemplary rule for determining light chain
      CDR-L3 motif
<220> FEATURE:
<221> NAME/KEY: MISC_FEATURE
<222> LOCATION: (3)..(3)
<223> OTHER INFORMATION: Xaa is any amino acid

<400> SEQUENCE: 21

Phe Gly Xaa Gly
1

<210> SEQ ID NO 22
<211> LENGTH: 4
<212> TYPE: PRT
<213> ORGANISM: Artificial Sequence
<220> FEATURE:
<223> OTHER INFORMATION: Exemplary rule for determining heavy chain
      CDR-H1motif
<220> FEATURE:
<221> NAME/KEY: MISC_FEATURE
<222> LOCATION: (2)..(4)
<223> OTHER INFORMATION: Xaa is any amino acid

<400> SEQUENCE: 22

Cys Xaa Xaa Xaa
1

<210> SEQ ID NO 23
<211> LENGTH: 5
<212> TYPE: PRT
<213> ORGANISM: Artificial Sequence
<220> FEATURE:
<223> OTHER INFORMATION: Exemplary rule for determining heavy chain
      CDR-H2motif

<400> SEQUENCE: 23

Leu Glu Trp Ile Gly
1               5

<210> SEQ ID NO 24
<211> LENGTH: 4
<212> TYPE: PRT
<213> ORGANISM: Artificial Sequence
<220> FEATURE:
<223> OTHER INFORMATION: Exemplary rule for determining heavy chain
      CDR-H3 motif
<220> FEATURE:
```

```
<221> NAME/KEY: MISC_FEATURE
<222> LOCATION: (3)..(3)
<223> OTHER INFORMATION: Xaa is any amino acid

<400> SEQUENCE: 24

Trp Gly Xaa Gly
1
```